US008754146B2

(12) United States Patent
Ziolkowski et al.

(10) Patent No.: US 8,754,146 B2
(45) Date of Patent: Jun. 17, 2014

(54) ANTIMICROBIAL QUATERNARY AMMONIUM ORGANOSILANE COMPOSITIONS

(75) Inventors: Nicoias Ziolkowski, Nivelles (BE); Jean-Paul Lecomte, Brussels (BE); Nathalie Wauthier, Naast (BE); Veronique Verhelst, Godarville (BE); Flore Vandemeulebroucke, Manage (BE)

(73) Assignee: Dow Corning Corporation, Midland, MI (US)

( * ) Notice: Subject to any disclaimer, the term of this patent is extended or adjusted under 35 U.S.C. 154(b) by 102 days.

(21) Appl. No.: 13/382,951

(22) PCT Filed: Aug. 13, 2010

(86) PCT No.: PCT/EP2010/004988
§ 371 (c)(1),
(2), (4) Date: Apr. 24, 2012

(87) PCT Pub. No.: WO2011/020586
PCT Pub. Date: Feb. 24, 2011

(65) Prior Publication Data
US 2012/0196953 A1 Aug. 2, 2012

(30) Foreign Application Priority Data
Aug. 15, 2009 (GB) .................................. 0914307.4

(51) Int. Cl.
*C09D 5/16* (2006.01)
*C04B 24/42* (2006.01)
(52) U.S. Cl.
USPC .............. 523/122; 514/63; 424/421; 427/214
(58) Field of Classification Search
None
See application file for complete search history.

(56) References Cited

U.S. PATENT DOCUMENTS

| 4,013,573 | A | | 3/1977 | Leikhim et al. |
| 4,851,047 | A | * | 7/1989 | Demlehner et al. ............... 524/4 |
| 4,921,701 | A | | 5/1990 | Blehm Blank |
| 4,985,023 | A | | 1/1991 | Blank et al. |
| 5,110,684 | A | * | 5/1992 | Cooper .......................... 428/447 |
| 5,209,775 | A | * | 5/1993 | Bank et al. ......................... 106/2 |
| 5,292,528 | A | | 3/1994 | Mori et al. |
| 6,268,423 | B1 | * | 7/2001 | Mayer et al. ................... 524/492 |
| 7,311,770 | B2 | | 12/2007 | Windridge et al. |
| 7,410,538 | B2 | | 8/2008 | Butler et al. |
| 8,445,560 | B2 | * | 5/2013 | Lecomte et al. ................... 524/5 |
| 2005/0204962 | A1 | * | 9/2005 | Luke et al. ..................... 106/813 |
| 2006/0217515 | A1 | | 9/2006 | Getman et al. |
| 2010/0119851 | A1 | * | 5/2010 | Giessler-Blank et al. .... 428/447 |
| 2010/0152332 | A1 | | 6/2010 | Lecomte et al. |
| 2010/0239784 | A1 | | 9/2010 | Owens |

FOREIGN PATENT DOCUMENTS

| EP | 0496510 A1 | | 7/1992 | |
| EP | 0575137 A1 | | 12/1993 | |
| EP | 0811584 A1 | | 12/1997 | |
| GB | 1433303 | * | 5/1974 | .............. C08K 9/06 |
| GB | 1433303 | | 4/1976 | |
| GB | 1433303 A | | 4/1976 | |
| JP | 2004-352617 A | | 12/2004 | |
| WO | WO 2004/105687 A2 | | 12/2004 | |
| WO | WO 2006/102366 A1 | | 9/2006 | |
| WO | WO 2006/102367 A1 | | 9/2006 | |
| WO | WO 2007/031775 A1 | | 3/2007 | |
| WO | WO 2008/062018 A1 | | 5/2008 | |
| WO | WO 2008062018 A1 | * | 5/2008 | .............. C04B 20/10 |

OTHER PUBLICATIONS

English language abstract and machine-assisted English translation for JP 2004-352617 extracted from the PAJ database on Aug. 21, 2013, 51 pages.
International Search Report for Application No. PCT/EP2010/004988 dated Jun. 24, 2011; 3 pages.

* cited by examiner

*Primary Examiner* — James J Seidleck
*Assistant Examiner* — Peter A Salamon
(74) *Attorney, Agent, or Firm* — Howard & Howard Attorneys PLLC

(57) ABSTRACT

Antimicrobial granules comprise carrier particles agglomerated by a binding agent containing a quaternary ammonium organosilane.

19 Claims, No Drawings

ANTIMICROBIAL QUATERNARY AMMONIUM ORGANOSILANE COMPOSITIONS

CROSS REFERENCE TO RELATED APPLICATIONS

This application is a U.S. national stage filing under 35 U.S.C. §371 of PCT Application No. PCT/EP10/004,988 filed on 13 Aug. 2010, currently pending, which claims the benefit of GB Patent Application No. 0914307.4 filed 15 Aug. 2009 under 35 U.S.C. §119 (a)-(d) and 35 U.S.C. §365(a). PCT Application No. PCT/EP10/004,988 and Patent Application No. 0914307.4 are hereby incorporated by reference.

This invention relates to antimicrobial compositions comprising a quaternary ammonium organosilane. By 'antimicrobial' we mean that the compositions kill or inhibit the growth of bacteria, fungi, viruses, moulds and/or algae. Many quaternary ammonium organosilanes are effective to inhibit the growth of all these microbes.

Quaternary ammonium organosilanes are useful as preservative agents for emulsions, dispersions or solutions in a medium where biological growth can be observed, for example in cosmetics, disinfectants, detergent compositions and coatings, in the production of textiles, pulp and paper, food, or oil and gas, and in wood preservation and building material protection.

Quaternary ammonium organosilanes have the advantage compared to most antimicrobial agents of resistance to diffusion or leaching, since the quaternary ammonium group is bound to an organosilane moiety. The quaternary ammonium organosilane remains at the surface to which it has been applied and thus has a longer effective life than other microbial agents such as other quaternary ammonium compounds.

There is however a need for antimicrobial quaternary ammonium organosilane compositions which can be applied to substrates more easily and safely. Quaternary ammonium organosilanes have a waxy solid form at room temperature; handling of such material is not easy. Quaternary ammonium organosilanes are also available in solution form but the usual solvent is methanol which is toxic and flammable.

U.S. Pat. No. 4,921,701 describes a colloidal suspension formed by combining a quaternary ammonium silane with a water soluble powder selected from antiperspirant salts, starches, clays and sugars. The suspension can be dried to a powder which will redissolve in water, forming a solution which releases the quaternary ammonium silane and which can be applied to a substrate.

U.S. Pat. No. 4,985,023 describes an antimicrobial superabsorbent formed of a cross-linked hydrophilic sodium salt form of a partially neutralized acrylic acid-based polymer gel having covalently bonded thereto a silane, for the purpose of providing the benefits of odour reduction, control of microbes and reduction of microbial rashes and allergies.

WO-A-2006/102366 describes in one aspect reacting an antimicrobial silicon-containing quaternary ammonium salt with a monomer or polymer containing functionality that will react with the silicon-containing quaternary ammonium salt to form a copolymer having sustained antimicrobial properties, and in a second aspect describes blending a solution of an antimicrobial polymerizable silicon-containing quaternary ammonium salt monomer with a second polymerisable monomer or with a polymer under conditions whereby the first silicon-containing quaternary ammonium salt monomer is polymerized to form a blended polymer. WO-A-2006/102367 relates to an antimicrobial polymer containing silicon-containing quaternary ammonium groups, which polymer can be made by the process of WO-A-2006/102366.

U.S. Pat. No. 7,410,538 describes a cementitious material in powder form comprising cement and a granulated hydrophobing additive, which comprises 5 to 15 parts by weight of an organopolysiloxane component, 10 to 50 parts by weight of a water-soluble or water-dispersible binder and 50 to 90 parts by weight of a carrier particle, to give from 0.01 to 5% by weight of the organosiloxane component based on the weight of the cement.

U.S. Pat. No. 7,311,770 describes a hydrophobic gypsum composition is provided which contains gypsum, a granulated hydrophobing additive and a pH effecting additive in an amount sufficient to maintain the pH of the composition in the range of 8 and 12.5, in the presence of water. The granule contains an organopolysiloxane having silicon bonded hydrogen, a water soluble or water dispersible binder, and a carrier, preferably gypsum or a stearate salt.

WO-A-2008/62018 describes cementitious materials which exhibit a hydrophobic character, and a granulated additive comprising an organosilicon component for rendering cementitious material hydrophobic. An emulsifier for the organosilicon component is deposited on the particulate carrier together with the organosilicon component and a binder to form the granulated additive.

According to the present invention antimicrobial granules comprise carrier particles agglomerated by a binding agent containing a quaternary ammonium organosilane. By 'agglomerated' we mean that carrier particles are combined into larger particles each comprising a plurality of carrier particles; these larger particles are termed 'granules'.

This invention also relates to a process for the preparation of antimicrobial granules comprising applying a liquid binding medium containing a dispersed quaternary ammonium organosilane to carrier particles and drying the carrier particles to which the liquid binding medium has been applied to agglomerate the carrier particles into granules. Alternatively the process can comprise applying simultaneously a liquid containing a dispersed quaternary ammonium organosilane and a liquid binding medium to the carrier particles prior to drying of the particles to agglomerate the carrier particles into granules.

The quaternary ammonium organosilane generally is of the formula

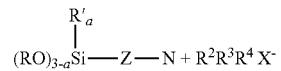

where each R represents an alkyl group having 1 to 4 carbon atoms; R' represents an alkyl group having 1 to 4 carbon atoms; a is 0, 1 or 2; Z represents an alkylene group having 1 to 4 carbon atoms; each of the groups $R^2 R^3$ and $R^4$ represents an alkyl or hydroxyalkyl group having 1 to 18 carbon atoms or an aralkyl radical having 7 to 10 carbon atoms; and X represents an anion. Two of the groups $R^2 R^3$ and $R^4$ may be joined to form a heterocyclic ring, or the $N+R^2R^3R^4$ moiety can be a pyridinium group.

In the quaternary ammonium organosilane of formula

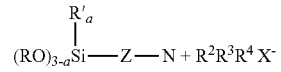

each R can be methyl, ethyl, propyl or butyl but is preferably methyl or ethyl. a is preferably 0, but R' if present is preferably methyl or ethyl. The alkylene group Z preferably has 3 or 4 carbon atoms, for example a 1,3-propylene, 2-methyl-1,3-propylene or 1,4-butylene group. $R^2$ is preferably a methyl or ethyl group; $R^3$ is preferably an alkyl group having 8 to 18 carbon atoms or an aralkyl group; and $R^4$ may be any alkyl or hydroxyalkyl group having 1 to 18 carbon atoms. The anion X can for example be chloride, bromide, fluoride, iodide, a sulphonate group, particularly an arylsulphonate group such as toluene-4-sulphonate, or acetate.

Examples of preferred quaternary ammonium organosilanes include

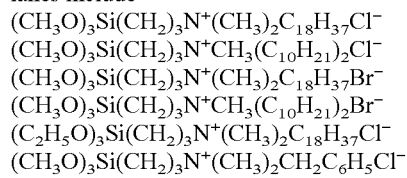

Further examples of suitable quaternary ammonium organosilanes include

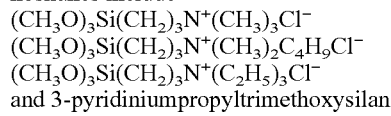

and 3-pyridiniumpropyltrimethoxysilane chloride.

The quaternary ammonium organosilane can be partially hydrolysed, that is some of the groups RO— can be HO— groups. The quaternary ammonium organosilane can be in pure monomeric form or can be partially condensed. The quaternary ammonium organosilane preferably retains an average of at least one silicon-bonded alkoxy group per silicon atom.

The carrier particles may be water-insoluble, water-soluble or water-dispersible. Suitable examples of carrier particles include silica, silicates, aluminosilicates, carbonates, sulfates and oxides. Examples of preferred silica particles include diatomaceous earth, calcined diatomaceous earth, quartz, sand and silica fume. Examples of preferred silicates and aluminosilicates include zeolite, metakaolin, feldspar, talc, sepiolite, wollastonites, phyllosilicates such as mica and clay materials such as bentonite. Examples of preferred carbonates include calcium carbonates, sodium carbonate, sodium bicarbonate, magnesium carbonate and dolomite. Examples of preferred sulfates include calcium sulfate, gypsum, sodium sulfate, magnesium sulfate and iron sulfate. Examples of preferred oxides and oxide materials include alumina, titanium dioxide, magnesium oxide, lime, cement, and calcium hydroxide, Further examples of suitable carrier particles include organic materials such as starch, rice starch, native starch, methyl cellulose, carboxy methyl cellulose, polystyrene beads, polyacrylate beads, sodium acetate, peat, wood flour, sugar and sugar derivatives, corn cob, and industrial products or by-products such as fly ash or slag. It is preferred that the carrier particles have a mean diameter of from 0.2 to 1000 μm, more preferably 0.2 to 50 μm, most preferably 1 to 10 μm.

For antimicrobial granules for use in a building material, it may be preferred to use materials which fulfill a useful role in the building material per se, for example in cementitious compositions the carrier particles can be aluminosilicates or cement itself, and in gypsum compositions the carrier particles can be gysum particles. Highly water-soluble carrier particles such as sodium carbonate, sodium bicarbonate, sodium sulfate or sugar are generally not suitable for use in a building material, but may be preferred for use in a cleaning composition.

The liquid binding medium from which the dispersed quaternary ammonium organosilane is applied to the carrier particles is preferably an aqueous solution of a binding agent which can be solidified by drying. The binding agent is preferably a polymer and is generally a film forming material which aids in binding the quaternary ammonium organosilane to the particulate carrier. The binder polymer can be either water-soluble or water-insoluble, that is it can be either dissolved or emulsified in water in the aqueous emulsion of the organosilicon component that is applied to the carrier. Such binder materials (either water soluble or water insoluble) are preferably materials which at room temperature, i.e. from 20 to 25° C., have a solid consistency. Examples of suitable water-soluble or water-dispersible binder materials include polyvinyl alcohols, methyl cellulose, carboxy methyl cellulose, polycarboxylates, cationic polymers, and other film forming polymers. Examples of suitable water-insoluble but water-dispersible (emulsifiable) binder materials include polymers such as polyvinyl acetate, vinyl acetate ethylene copolymers and acrylate ester polymers. Blends of binder material as described above can be used, for example a blend of a water-soluble binder polymer such as polyvinyl alcohol with a water-insoluble binder polymer such as polyvinyl acetate. Water dispersion of the resultant granules may be facilitated by the appropriate blend of water soluble and water insoluble binder material.

Cationic polymer binders may have particular advantages for applications such as laundry and textile treatment to enhance the deposition of the quaternary ammonium organosilane on the fabrics being laundered or textile being treated. Examples of suitable cationic polymer binders include polymers comprising dialkylaminoalkyl acrylate, dialkylaminoalkyl methacrylate, monoalkylaminoalkyl acrylate, monoalkylaminoalkyl methacrylate, trialkyl methacryloxyalkyl ammonium salt, trialkyl acryloxyalkyl ammonium salt, or diallyl quaternary ammonium salt units, and/or pyridinium, imidazolium, or quaternised pyrrolidine units, Further examples of preferred binders are waxes, preferably waxes having a melting point in the range 30 to 100° C., more preferably 40 to 90° C. Examples of waxes are petroleum-derived waxes such as paraffin wax or microcrystalline wax, carboxylic ester waxes, polyether waxes and fatty (long chain) acids, fatty alcohols, fatty amines, fatty amides, ethoxylated fatty acids or fatty alcohols, and long chain alkyl phenols. Preferred waxes include ethoxylated fatty alcohol based waxes and ethoxylated fatty alcohol wax/C16-20 fatty acid mixtures. The preferred fatty acid is stearic acid.

A waxy binder can be applied from aqueous solution or suspension as described above, or can alternatively be applied to the carrier particles in the molten state and solidified by cooling. The quaternary ammonium organosilane can be dissolved or dispersed in the molten waxy binder.

When the antimicrobial granules are for use in a cementitious building material, the water solubility of the binder material should preferably be sufficient that it does not interfere with the hydration process of the cementitious material when water is added to the cementitious material prior to its application or use.

The particulate carrier and the binding agent are preferably chosen to be unreactive with the quaternary ammonium organosilane, so that there is no chemical reaction between the cationic silane and any other ingredient of the antimicrobial granules. This ensures that a quaternary ammonium organosilane registered as a biocide remains chemically unchanged in the granulated formulation.

The quaternary ammonium organosilane and binding agent can be applied to the particulate carrier from aqueous emulsion. The emulsifier present can for example be a non-ionic, anionic, cationic or amphoteric emulsifier, although non-ionic emulsifiers are preferred. Examples of non-ionic emulsifiers include polyvinyl alcohol, ethylene oxide propylene oxide block copolymers, alkyl or alkaryl polyethoxylates in which the alkyl group has 8 to 18 carbon atoms, alkyl polyglycosides or long chain fatty acids or alcohols. Some water-soluble polymers such as polyvinyl alcohol can thus act as both binder polymer and emulsifier. In some preferred emulsions polyvinyl alcohol acts as emulsifier and also as part of the binder polymer together with a water-insoluble polymer such as polyvinyl acetate. Examples of anionic surfactants include alkali metal and ammonium salts of fatty acids having 12 to 18 carbon atoms, alkaryl sulphonates or sulphates and long chain alkyl sulphonates or sulphates. Examples of cationic surfactants include quaternary ammonium salts containing at least one long chain alkyl group having 8 to 20 carbon atoms.

The quaternary ammonium organosilane can alternatively be dissolved in a water miscible organic solvent such as ethanol or isopropanol before being mixed with a binding agent and applied to the carrier particles, but this process is not preferred because of the need to prevent the water miscible organic solvent escaping into the environment.

The liquid binding medium containing the dispersed quaternary ammonium organosilane is deposited, for example by spraying, onto the carrier particles, for example in a fluidised bed. The treated carrier particles are dried, preferably while still fluidized, to solidify the binding agent and quaternary ammonium organosilane in admixture onto the carrier particles so that carrier particles are agglomerated to larger particles which form a free flowing powder. Spraying of the liquid binding medium containing the dispersed quaternary ammonium organosilane onto a fluidized bed of carrier particles, followed by drying, can be carried out batchwise but is preferably carrier out continuously. For example the liquid binding medium containing dispersed quaternary ammonium organosilane can be sprayed into a tower through which the carrier particles fall. Alternatively a liquid binding medium and a liquid containing dispersed quaternary ammonium organosilane can be sprayed onto the carrier particles from separate spray nozzles in such a tower. Solidification may be encouraged by the use of air counter current to aid evaporation of any solvent present. Total solidification should not take place prior to the liquid binding medium being deposited onto the carrier particles. The tower can for example be a vertical continuous granulating mixer comprising a shaft fitted with blades rotating within a tubular housing and having an inlet for carrier particles and a spray inlet for liquid above the blades so that the liquid binding medium containing dispersed quaternary ammonium organosilane contacts the carrier particles above the blades. The granulated antimicrobial additive is then collected at the bottom of the tower.

In another granulation method an emulsion of quaternary ammonium organosilane and a liquid binder polymer are sprayed simultaneously into a drum mixer containing the carrier particles, or an emulsion of quaternary ammonium organosilane in a solution of binder polymer is sprayed into a drum mixer containing the carrier particles. The spray droplets partially evaporate on contact with the carrier particles. After mixing, the particles are transferred to a fluidised bed where evaporation is completed with ambient air. The granulated antimicrobial additive can be collected from the fluidised bed. Granulation methods are also described in a number of patent specifications including EP-A-811584 and EP-A-496510.

When a wax binder is applied as a melt to the carrier particles, granulation can be achieved by cooling the mixture of wax binder, quaternary ammonium silane and carrier particles. The mixture can for example be cooled in a fluidized bed, or the molten wax binder containing quaternary ammonium silane can be sprayed into a tower through which the carrier particles fall. Such a tower may have rotating blades as described above and optionally an updraft of cold air to aid in solidifying the molten wax.

Typical apparatus which is useful for granulation includes the Eirich® pan granulator, the Schugi® mixer, the Paxeson-Kelly® twin-core blender, the Lödige® ploughshare mixer or one of the numerous types of fluidised bed apparatuses, e.g. Aeromatic® fluidised bed granulator.

The antimicrobial granules are preferably in the size range 0.1 to 2.0 mm. In many of the above apparatus the granules produced are predominantly in this size range. Larger particles may be produced in the granulating apparatus; such larger particles can then be crushed and screened by sieving to produce antimicrobial granules of hydrophobing additive of the desired size.

Organopolysiloxanes and/or organosilanes which do not include quaternary ammonium groups can be included in the antimicrobial granules together with the quaternary ammonium organosilane. Such organopolysiloxanes and/or organosilanes can be chosen to bring benefits to the targeted application such as hydrophobicity, reinforcement, or adhesion. The organopolysiloxane can for example be a linear volatile polydimethylsiloxane, a cyclic volatile polydimethylsiloxane, an alkylmethylpolysiloxane, a silicone oil, an organopolysiloxane resin, a organopolysiloxane elastomer, an organopolysiloxane gum, a silicone acrylate, a silicone carbinol fluid, a silicone polyether, a non-volatile polydiorganosiloxane, a saccharide-siloxane copolymer, a sulfonated organopolysiloxane, or a combination of two or more of these. The organosilane can for example be an alkyltrialkoxysilane, dialkyldialkoxysilane, trialkylalkoxysilane, epoxyalkyltrialkoxysilane, methacryloxyalkyltrialkoxysilane or acryloxyalkyltrialkoxysilane or a combination of two or more of these.

Organopolysiloxanes, and some organosilanes, are known as hydrophobing additives for cementitious products, gypsum products and other building materials. Such hydrophobing organosilicon additives can be incorporated in the granules of the invention to produce granules which are both antimicrobial and hydrophobing, particularly if the antimicrobial granules are for use in building materials. The hydrophobing organosilicon additive is generally applied to the carrier particles from a liquid medium together with the quaternary ammonium organosilane. The hydrophobing organosilicon additive and the quaternary ammonium organosilane can for example be emulsified together in an aqueous solution of a binding agent and sprayed onto the carrier particles.

Examples of organosilanes which are useful as hydrophobing additives in building materials include alkylalkoxysilanes containing an alkyl group having at least 3, for example 8 to 18 carbon atoms. The hydrophobing organosilane is preferably a dialkoxysilane or trialkoxysilane. Examples of such organosilanes are n-octyl trimethoxysilane, 2-ethylhexyl triethoxysilane and n-octyl triethoxysilane.

Examples of organopolysiloxanes which are useful as hydrophobing additives in building materials include polydimethylsiloxane (PDMS) and polydiorganosiloxanes which comprise methylalkylsiloxane units in which the said alkyl group contains 2-20 carbon atoms, particularly those in which the said alkyl group contains 6-20 carbon atoms, for example a dimethyl methyloctyl siloxane copolymer sold by Dow Corning under the trade name DOW CORNING® BY 16-846 FLUID. Some of the alkyl groups of the organopolysiloxane can be substituted by a trialkoxysilyl moiety to provide appropriate reactivity of the resultant organosiloxane component towards cementitious materials, for example the organosiloxane can be the trimethylsiloxy and alkoxy-terminated dimethyl methylalkyl siloxane copolymer sold by Dow Corning under the trade name DOW CORNING® BY 16-606.

The antimicrobial granules can if desired contain both an organosilane hydrophobing additive and an organopolysiloxane hydrophobing additive.

Similarly organopolysiloxanes such as polydiorganosiloxanes and amino-functional organopolysiloxanes are widely used as softening agents in laundry compositions and in textile finishing. Such softening agents can be incorporated in the granules of the invention to produce granules which are both antimicrobial and softening, for example for use in laundry washing powders or in textile finishing compositions sold in powder form. The organopolysiloxane softening agent can be applied to the carrier particles from a liquid medium together with the quaternary ammonium organosilane.

The antimicrobial granules preferably comprise 40 to 95% by weight particulate carrier, from 1 to 20% by weight binder polymer, from 0.2, usually from 0.5 or 1, up to 30 or 40% by weight quaternary ammonium organosilane and from 0 to 40% by weight (preferably 5 to 35% when present) organosilicon hydrophobing agent or organopolysiloxane softening agent.

Although it is preferred that the antimicrobial granules consist only of the carrier particles, binder, quaternary ammonium organosilane and optionally the organosilicon hydrophobing agent or organopolysiloxane softening agent, additional ingredients may be included, for example viscosity modifiers, pigments, colorants, preservatives, gelling agents, pH modifiers, buffers, accelerators, or retarders. It is however preferred that such additional optional ingredients do not comprise more than 5% by weight of the total weight of the granules.

The antimicrobial granules of the invention can be used in eliminating and preventing microbiological contamination and deterioration of surfaces of buildings and walls, and preventing alteration and biodeterioration of various construction materials, particularly cementitious materials such as mortars, grouts, and sealants and gypsum products such as plaster. The invention includes a cementitious or gypsum building material containing antimicrobial granules according to the invention as defined above. The antimicrobial granules are preferably present in the building material in an amount such that from 0.001 to 0.5% by weight of the quaternary ammonium organosilane is present based on the dry weight of cement or gypsum. More preferably the amount of antimicrobial granules is preferably from 0.01 to 5% by weight of dry cement or gypsum and the amount of quaternary ammonium organosilane is 0.002 to 1% by weight based on the dry weight of cement or gypsum.

The antimicrobial granules of the invention have the advantage that addition of the granules to a cementitious or gypsum building material can conveniently be carried out by dry mixing the antimicrobial granules with the building material at the stage where the building material is in a dry, powdery form. Alternatively the antimicrobial granules can be added during or after hydration of the cement or gypsum, for example immediately prior to or during the process of applying a cementitious material to a substrate.

Because the quaternary ammonium organosilane is contained in the binding agent of the granules rather than the carrier of the granules, the quaternary ammonium organosilane is not necessarily associated with the carrier after the granules have been incorporated in the building material. The quaternary ammonium organosilane, which is hydrophobic, is concentrated at the surface of the building material, where it is most effective. The carrier particles are more evenly dispersed throughout the building material. This is an advantage compared to coating an antimicrobial agent directly on a carrier or reacting the antimicrobial agent with the carrier, in which case the carrier appears with the antimicrobial agent at the substrate surface and may detract from the surface appearance.

The binding agent can also be chosen to become more evenly dispersed throughout the building material, for example a water-soluble or water-dispersible binder can be used when the granules are for a building material such as cement or gypsum which is to be hydrated.

The antimicrobial granules of the invention can also be used as preservative agents for emulsions, dispersions or solutions in a medium where biological growth can be observed, in cosmetics, disinfectants, detergents, textiles, pulp and paper, packaging, wood preservation, water treatment, water transportation, food, oil and gas, and coatings. The antimicrobial granules can be used in preventing biodeterioration of substrates such as fabrics. Such biodeterioration can be easily observed by the presence of black spots at the surface of materials. The contamination can take the form of visible surface growth, discoloration, or bad odor. Molds are detrimental for health; they cause eye, skin and respiratory tract irritation. They can be poisonous if ingested or inhaled.

Examples of fabrics to which the antimicrobial granules can be applied include woven, knitted or nonwoven fabrics for use in carpets, synthetic sports field surfaces, socks, filtration media, bed sheets, blankets, bedspreads, draperies, fire hoses, humidier belts, mattress pads, mattress ticking, underwear, disposable diapers, outerwear, hosiery, roofing materials, sand bags, tents, tarpaulins, sails, rope, athletic and casual shoes, shoe insoles, toilet seat covers, throw rugs, towels, umbrellas, upholstery fiberfill, intimate apparel, and wiping cloths. The antimicrobial granules are in a convenient form for weighing and handling and can be applied to fabric from aqueous solution, for example they can be added to water used for washing or cleaning the fabric or to any aqueous solution which is used in finishing a fabric. The granules apply the quaternary ammonium organosilane to the surface of the fabric without the quaternary ammonium organosilane being permanently bonded to the carrier of the granules, so that the quaternary ammonium organosilane can bind to the fabric surface.

For use in products which are sold in powder form, for example laundry washing powders, the antimicrobial granules can readily be mixed with the powder product. The antimicrobial granules are valuable in laundry products, whether in powder or liquid form, which are designed for use at low temperature. Low temperature washing products are often preferred to save energy, and washing products have been devised which are effective at removing dirt at low temperature. The antimicrobial granules help in killing bacteria which would be destroyed by high temperature washing but might survive low temperature washing. The antimicrobial granules can also be used in cleaning products for hard surfaces such as ceramic tiles.

The antimicrobial granules of the invention can be incorporated in plastics material which is to be extruded or otherwise moulded, for example to make piping, toilet tanks, shower curtains or packaging. Use of the antimicrobial granules in packaging gives extra antimicrobial protection to the product packaged and may allow reduction of the amount of preservative in the product itself.

The antimicrobial granules can also be incorporated in wallpaper including vinyl paper, in polyurethane cushions or in medical devices.

The antimicrobial granules of the invention have safety and handling advantages over known forms of quaternary ammonium organosilane. The antimicrobial granules, even with a high quaternary ammonium organosilane content of up to 30% by weight, have a flashpoint of over 200° C., whereas the known liquid forms of quaternary ammonium organosilane have a flashpoint of about 20° C. Granules also have reduced skin contact risk and reduced risk of release to the environment, since a spilt solid can easily be recovered. The quaternary ammonium organosilane in granular form is also less likely to lose effectiveness by hydrolysis or condensation of the quaternary ammonium organosilane in water.

The invention is illustrated by the following Examples, in which parts and percentages are given by weight unless otherwise indicated.

EXAMPLE 1

3.9 g of octadecyldimethyltrimethoxysilylpropyl ammonium chloride sold under the Trade Mark ÆGIS Microbe Shield®—AEM 5772 was mixed with 24.9 g of n-octyltriethoxysilane. 25.2 g of hydroxyl-terminated polydimethylsiloxane was added, drop by drop, to 50 g of a 20% solution of polyvinyl alcohol sold under the Trade Mark Mowiol 4/88. The mix of quaternary ammonium organosilane and n-octyltriethoxysilane was mixed into the emulsion. 56.2 g of the resulting emulsion was sprayed onto 120 g of zeolite NA of particle size about 2 to 5 µm, causing the zeolite particles to adhere as granules. The obtained granules were then dried in a fluidized bed and after drying were crushed in a Grindomix® during 4 seconds at 8000 rpm so as to achieve the desired granule size of 0.2 to 0.5 mm. The granules contained 1.0% of the octadecyldimethyltrimethoxysilylpropyl ammonium chloride.

54 g of sand, 18 g of Portland cement and 0.5 g of the granules of Example 1 were dry mixed. 9.5 g of water was added and mixed to form mortar. The mixture was placed in a plastic mold to make mortar blocks of size 7 cm×7 cm×3 cm. Blocks of mortar are allowed to cure during 7 days, in a controlled atmosphere (100% relative humidity (RH) at room temperature).

COMPARATIVE EXAMPLE C1

37.5 g of hydroxyl-terminated polydimethylsiloxane was added, drop by drop, to 75 g of 20% polyvinyl alcohol Mowiol 4/88 solution to form an emulsion. 37.5 g of n-octyltriethoxysilane was added to the emulsion. 42.1 g of the resulting emulsion was sprayed onto 80 g of zeolite NA. The obtained granules were dried and crushed as described in Example 1 to form hydrophobing granules of particle size 0.2 to 0.5 mm. 0.5 g of the granules were used in making mortar blocks as described in Example 1.

COMPARATIVE EXAMPLE C2

54 g of sand, 18 g of Portland cement, 0.5 g of the granules of Comparative Example C1 and 0.05 g ÆGIS Microbe Shield®—AEM 5772 octadecyldimethyltrimethoxysilylpropyl ammonium chloride were dry mixed. 9.5 g of water was added and mixed to form mortar, which was made into mortar blocks as described in Example 1.

COMPARATIVE EXAMPLE C3

98 g Zeolite NA was coated with 3 g ÆGIS Microbe Shield®—AEM 5772 octadecyldimethyltrimethoxysilylpropyl ammonium chloride. 54 g of sand, 18 g of Portland cement, 0.5 g of the granules of Comparative Example C1 and 0.5 g of the zeolite coated with quaternary ammonium silane were dry mixed. 9.5 g of water was added and mixed to form mortar, which was made into mortar blocks as described in Example 1.

The mortar blocks of Example 1 and Comparative Examples C1 to C3 were tested for antimicrobial activity and resistance to water uptake. Mortar blocks prepared by the process described in Example 1 but without any additive were also tested.

The antimicrobial testing is based on the fungistatic activity which was measured by the ISO 846 test method. The mortar blocks were exposed to the action of selected strains of fungi for a certain period of time (28 days) under specific conditions of temperature (28±1° C.) and humidity (90%). The resistance against fungus growth is assessed by visual and stereomicroscopic examinations. The fungal growth was rated with a scale from 0 to 5:

0—No growth apparent under the stereomicroscope
1—No growth visible to the naked eye, but clearly visible under a stereomicroscope
2—Growth visible to the naked eye, covering up to 25% of the test surface
3—Growth apparent to the naked eye, covering up to 50% of the test surface
4—Considerable growth, covering more than 50% of the test surface
5—Heavy growth, covering the entire test surface.

The results of antimicrobial testing are given in Table 1.

The antimicrobial tests were carried out on fresh samples cured as described above, and also on samples which had been aged for 28 days at 35° C. and 70% R.H. Before being tested, each mortar block was dried for 24 h at 50° C. in an oven.

TABLE 1

| Example | Growth rating (fresh sample) | Growth rating (aged sample) |
|---|---|---|
| 1 | 1 | 1 |
| C1 | 3 | 3 |
| C2 | 3 | 1 |
| C3 | 1 | 1 |
| Untreated mortar | 3 | 3 |

The antimicrobial testing shows that mortar treated with neat n-octyl triethoxysilane (C1), which is a water repellent only, does not prevent biological growth compared to untreated mortar. Mortar treated with n-octyl triethoxysilane and quaternary ammonium silane added separately (C2) showed some antimicrobial effect, but this was less than the granules of Example 1 or zeolite coated with quaternary ammonium silane (C3).

In the hydrophobic performance tests, the weighed dried mortar block samples were immersed in water with a height of water 3 cm above the top of the sample. After 1, 3, 24 and 72 hours, the samples were removed from water. Excess water was wiped from the samples, and each sample was weighed. The mass of water absorbed by the samples was calculated and the percentage of water absorbed (relative to the weight of the dry blocks) is quoted in Table 2.

TABLE 2

| Example | % water 1 hour | % water 3 hours | % water 24 hours | % water 72 hours |
|---|---|---|---|---|
| 1 | 1.0 | 1.8 | 3.8 | 4.8 |
| C1 | 0.4 | 0.7 | 1.9 | 2.5 |
| C2 | 0.7 | 1.1 | 2.9 | 4.5 |
| C3 | 1.2 | 2.0 | 4.6 | 6.5 |
| Untreated mortar | 3.5 | 4.7 | 5.7 | 5.9 |

The results in Table 2 show that n-octyl triethoxysilane improves the hydrophobic performance, that is it lowers the water uptake. Table 2 also shows the impact of quaternary ammonium silane on water uptake when added to the n-octyl triethoxysilane. In every case, it is lowering the hydrophobic performance but for Example 1 (and comparative example C2) the water uptake is still acceptable and is still considerably less than the water uptake of untreated mortar. The addition of zeolite coated with the quaternary ammonium silane (C3) substantially increases the water uptake of the mortar, so that after 72 hours it is higher than the water uptake of untreated mortar.

The physical appearance and handling properties of the mortar blocks of Example 1 and Comparative Examples C1 to C3 were compared to the mortar block made from untreated mortar and rated from 1 to 5 on the following scale:

0 Kinetic impact of the additive on mortar blocks: cement paste has not cured
1 Redhibitory impact of the additive on the physical properties of mortar blocks: Cement paste has cured but lead to poor physical properties of the mortar blocks (very porous and friable)
2 Visual impact of the additive on the physical properties of the mortar blocks: more macro porosity than untreated mortar block
3 Aesthetic impact of the additive on mortar blocks: difference of color between untreated and treated mortar
4 Aesthetic impact of the additive on mortar blocks: presence of stains
5 No seen impacts of additive on mortar blocks

TABLE 3

| Example | Qualitative rating of mortar block | remark |
|---|---|---|
| 1 | 5 | No significant changes between untreated and treated mortars |
| C1 | 5 | No significant changes between untreated and treated mortars |
| C2 | 1 | The treated mortar block was much more porous and friable than the untreated mortar block |
| C3 | 4 | Presence of white stains |
| Untreated mortar | 5 | |

The results in Table 3 show that an addition of an additive can have a deleterious impact on physical properties of mortar. For example, the addition of neat quaternary ammonium silane as in Comparative Example C2 has a deleterious impact; the mortar block of C2 is much more porous and friable than the untreated mortar block or the mortar block of Example 1. The fact that the mortar block of C2 is friable makes that product unsuitable for construction applications.

Table 3 also shows the aesthetic impact of quaternary ammonium silane coated onto zeolite as in Comparative Example C3 is poor. White stains due to zeolite are visible in the mortar block of C3, probably due to bad dispersion of the product in the cement paste.

The bulk powder properties of the granules of Example 1 and the granules of comparative example C3 were tested by a jolting volumeter STAV 2003 according to DIN ISO 787 Teil 11 and ASTM B 527-70. The poured density of the granules is calculated from the initial height of the granules after they have been poured into the volumeter. Tapping is then carried out, and the height of granules is measured after 100 and 500 taps, and hence the tapped density. The compressibility and the cohesivity of the powder or granules is determined in the DIN test by the Hausner ratio, which is the ratio of the tapped density to the loose (poured) density. A Hausner ratio between 1.0 and 1.2 shows that the bulk powder is slightly compressible and cohesive, whilst a Hausner ratio between 1.2 and 1.4 shows that the bulk powder is compressible and cohesive. The flowability is determined in the ASTM test by the Carr index, which is the ratio of the (tapped density minus poured density) to poured density. A Carr index of below 0.15 shows good flowability, whilst a Carr index above 0.25 shows bad flowability. The results are shown in Table 4.

TABLE 4

| | Example 1 | Comparative example C3 |
|---|---|---|
| Mass | 74.0 g | 35.3 g |
| Initial height | 14.4 cm | 9.6 cm |
| 100 tap height | 12.4 cm | 8.5 cm |
| 500 tap height | 11.9 cm | 6.7 cm |
| Poured density | 505 kgm$^{-3}$ | 361 kgm$^{-3}$ |
| Tapped density 100 taps | 586 kgm$^{-3}$ | 408 kgm$^{-3}$ |
| Tapped density 500 taps | 611 kgm$^{-3}$ | 518 kgm$^{-3}$ |
| Carr index 100 taps | 0.14 | 0.11 |
| Carr index 500 taps | 0.17 | 0.30 |
| Hausner ratio 100 taps | 1.16 | 1.13 |
| Hausner ratio 500 taps | 1.21 | 1.43 |

The jolting volumeter testing shows that the granules of Example 1 have a better flowability than the zeolite coated with the quaternary ammonium silane.

EXAMPLE 2

50 g of quaternary ammonium silane Æ EGIS Microbe Shield® AEM5772 was emulsified in 50 g of 20% aqueous polyvinyl alcohol Mowiol 4/88 solution. 49 g of the emulsion was sprayed onto 100 g of zeolite, The obtained granules were then dried in a fluidized bed. The granules obtained after the drying step were crushed in a Grindomix® for 4 seconds at 8000 rpm so as to achieve the desired particle size of 0.2 to 0.5 mm.

0.69 g of the granules of Example 2 were added to 100 g of soft water in a linitest tank. A 5×5 cm cotton fabric piece was added to the linitest tank and treated for 30 minutes at 30° C. with an agitation of 45 rpm. The cotton fabric was then let to air dry for 1 night.

The antimicrobial performance of a treated cotton fabric can be predicted based on the bromophenol blue analysis. In this test a drop of an aqueous sodium salt of bromophenol blue is applied to the dried treated fabric. The anion of bromophenol blue can be complexed with the cation of a quaternary ammonium silane while it is on a substrate. The blue colored complex formed is qualitatively indicative of the presence of the cation on the substrate thus indicating the extent of antimicrobial agent on a given substrate. A comparison of the intensity of retained blue color to a color standard is used to determine the amount of quaternary ammonium silane at the fabric surface. The shape of the blue drop on the fabric is also visually assessed on a scale of 0 (weak colour, drop spread throughout fabric) to 10 (intense colour, small round drop). An intense blue colour and a neat round drop indicate a high level of readily available antimicrobial quaternary ammonium silane. The results of such a test on the fabric treated according to Example 2 is given in Table 4, together with a comparative test (C4) in which ÆEGIS Microbe Shield® AEM5772 as sold commercially was applied to the fabric.

COMPARATIVE EXAMPLE C5

4.8 g of quaternary ammonium silane ÆEGIS Microbe Shield® —AEM 5700 (octadecyldimethyltrimethoxysilylpropyl ammonium chloride diluted in methanol) was added to 115 g of water. 15 g of aluminium zirconium salt was added and mixed together at 30° C., 200 rpm for 25 minutes. This comparative example is based on Example 2 of U.S. Pat. No. 4,921,701. The final preparation was air dried so as to remove water and methanol. The dry product was crushed to obtain the desired particle size of 0.2 to 0.5 mm. The product was tested as described in Example 2.

The fabrics tested were subjected to two ageing steps. Each ageing step comprised 25 minutes immersion in water at 30° C. in the linitest tank, followed by drying and reassessment of the fabric. The results are shown in Table 5

TABLE 5

| Example | % active | Amount added | Initial colour rating | Initial drop shape | Colour rating 1 ageing | Drop shape 1 ageing | Colour rating 2 ageings | Drop shape 2 ageings |
|---|---|---|---|---|---|---|---|---|
| 2 | 14.4 | 0.69 g | 9 | 8 | 9 | 8 | 9 | 7 |
| C4 | 72 | 0.10 g | 7 | 5 | 7 | 5 | 7 | 5 |
| C5 | 13.8 | 0.72 g | 5 | 5 | 2 | 0 | 0 | 0 |

It can be seen from Table 4 that the quaternary ammonium silane applied by the granules of Example 2 is securely located on the fabric compared to comparative examples C4 and C5. In particular the antimicrobial quaternary ammonium silane remains effective on the fabric after two immersions in water, unlike the quaternary ammonium silane applied by the process of C5.

EXAMPLE 3

75 g of quaternary ammonium silane ÆEGIS Microbe Shield® AEM5772 was emulsified in 75 g of 20% aqueous polyvinyl alcohol Mowiol 4/88 solution. 95.5 g of the emulsion was sprayed onto 100 g of calcined diatomaceous earth. The obtained granules were then dried in a fluidized bed. The granules obtained after the drying step were crushed in a Grindomix® for 4 seconds at 8000 rpm so as to achieve the desired particle size of 0.2 to 0.5 mm.

The flash points of the granules of Examples 2 and 3 were measured by the closed cup method.
Flash point of Example 2: >200° C.
Flash point of Example 3: >150° C.
By comparison, the flash point of ÆEGIS Microbe Shield® AEM5772 is 22° C.

The invention claimed is:

1. Antimicrobial granules comprising carrier particles agglomerated by a binding agent containing a quaternary ammonium organosilane.

2. Antimicrobial granules according to claim 1 wherein the carrier particles are selected from silica, silicate, aluminosilicate, carbonate, sulfate and oxide particles.

3. Antimicrobial granules according to claim 2 wherein the carrier particles are zeolite particles.

4. Antimicrobial granules according to claim 1 wherein the mean particle size of the carrier particles is in the range 1 to 10 µm.

5. Antimicrobial granules according to claim 1 wherein the mean particle size of the granules is in the range 0.1 to 2.0 mm.

6. Antimicrobial granules according to claim 1 wherein the binding agent is a water-soluble or water-dispersible polymer selected from polyvinyl alcohols, methyl cellulose, carboxy methyl cellulose, polycarboxylates, and cationic polymers.

7. Antimicrobial granules according to claim 1 wherein the binding agent is an emulsifiable water-insoluble polymer selected from polyvinyl acetate, vinyl acetate ethylene copolymers and acrylate ester polymers.

8. Antimicrobial granules according to claim 1 wherein the quaternary ammonium organosilane is of the formula

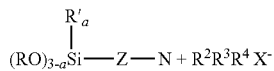

where each R represents a methyl or ethyl group; a is 0, 1 or 2; R' if present represents a methyl or ethyl group; Z represents an alkylene group having 3 or 4 carbon atoms; $R^2$ represents a methyl or ethyl group; $R^3$ represents an alkyl group having 8 to 18 carbon atoms or an aralkyl group; $R^4$ represents an alkyl or hydroxyalkyl group having 1 to 18 carbon atoms; and X represents an anion selected from chloride, bromide, fluoride, iodide, an arylsulphonate anion and acetate.

9. Antimicrobial granules according to claim 1 wherein the quaternary ammonium organosilane content of the granules is in the range 0.5 to 30% by weight.

10. Antimicrobial granules according to claim 1 wherein the binding agent further contains an organosilane or organopolysiloxane having no amine or quaternary ammonium functionality.

11. Antimicrobial granules according to claim 10 wherein the organosilane having no amine or quaternary ammonium functionality is a hydrophobic alkylalkoxysilane containing an alkyl group having at least 3 carbon atoms.

12. A process for the preparation of antimicrobial granules comprising applying a liquid binding medium containing a dispersed quaternary ammonium organosilane to carrier particles and solidifying the carrier particles to which the liquid binding medium has been applied to agglomerate the carrier particles into granules.

13. A process for the preparation of antimicrobial granules comprising simultaneously applying a liquid containing a dispersed quaternary ammonium organosilane and a liquid binding medium to carrier particles and drying the carrier particles to which the liquid binding medium has been applied to agglomerate the carrier particles into granules.

14. A process according to claim 12 wherein the liquid binding medium is an aqueous solution of a binding agent.

15. A process according to claim 14 wherein the binding agent is polyvinyl alcohol.

16. A process according to claim 12 wherein the quaternary ammonium organosilane is emulsified in the solution of binding agent.

17. A process according to claim 12 wherein the process further comprises spraying the liquid binding medium containing dispersed quaternary ammonium organosilane onto the carrier particles.

18. A process according to claim 12 wherein the drying of the carrier particles to which the liquid binding medium containing the dispersed quaternary ammonium organosilane has been applied is carried out in a fluidized bed.

19. A cementitious or gypsum building material comprising cement or gypsum and antimicrobial granules according to claim 1.

* * * * *